(12) United States Patent
Kosasky et al.

(10) Patent No.: US 6,575,021 B1
(45) Date of Patent: Jun. 10, 2003

(54) SAMPLE SURFACE COMPONENT FOR AN INSTRUMENT THAT MEASURES VISCOSITY AND VISCOELASTICITY

(75) Inventors: Harold J. Kosasky, Chestnut Hill, MA (US); Elias G. Noukas, Milford, NH (US); Paul D. Murray, Carlisle, MA (US); Alfredo O. Kenig, Carlisle, MA (US)

(73) Assignee: Boston Rheology, Inc., Chestnut Hill, MA (US)

( * ) Notice: Subject to any disclaimer, the term of this patent is extended or adjusted under 35 U.S.C. 154(b) by 30 days.

(21) Appl. No.: 10/120,199

(22) Filed: Apr. 10, 2002

(51) Int. Cl.[7] .......................... A61B 10/00; G01N 3/08; G01N 33/16; G01N 3/56
(52) U.S. Cl. ...................... 73/54.37; 73/54.22; 73/54.02
(58) Field of Search ............................. 73/54.37, 54.39, 73/54.22, 64.49, 54.02

(56) References Cited

U.S. PATENT DOCUMENTS

| | | | | |
|---|---|---|---|---|
| 3,368,390 A | * | 2/1968 | Norcross | 73/56 |
| 3,387,490 A | * | 6/1968 | Wise | 73/101 |
| 3,979,945 A | | 9/1976 | Kopito et al. | 73/60 |
| 3,982,423 A | | 9/1976 | Schuster | 73/54 |
| 4,002,056 A | | 1/1977 | Kopito et al. | 73/53 |
| 4,059,986 A | * | 11/1977 | Schuster | 73/54 |
| 4,167,110 A | * | 9/1979 | Kopito et al. | 73/58 |
| 4,343,190 A | * | 8/1982 | Danko et al. | 73/846 |
| 4,466,271 A | * | 8/1984 | Geromiller | 73/10 |
| 4,779,627 A | | 10/1988 | Kosasky | 128/738 |
| 5,052,219 A | * | 10/1991 | Fery et al. | 73/54.39 |
| 5,079,956 A | * | 1/1992 | Burhin et al. | 73/846 |
| 5,640,968 A | | 6/1997 | Kosasky | 128/738 |
| 5,788,649 A | | 8/1998 | Kosasky | 600/551 |
| 5,851,190 A | | 12/1998 | Kosasky | 600/551 |
| 6,149,604 A | | 11/2000 | Kosasky | 600/551 |

OTHER PUBLICATIONS

L. E. Kopito et al., "The Tackiness Rheometer Determination of Viscoelasticity of Cervical Mucus," Human Ovulation, Elsevier North–Holland Biomedical Press, 1979, pp. 351–361.

Gerald Oster et al., "Cyclic Variation of Sialic Acid Content in Saliva," American Journal of Obstetrics and Gynocology, vol. 114, No. 2, pp. 190–193 (Sep. 15, 1972).

* cited by examiner

Primary Examiner—Hezron Williams
Assistant Examiner—David J. Wiggins
(74) Attorney, Agent, or Firm—Morse, Altman & Martin

(57) ABSTRACT

A sample surface component for an instrument the measures viscosity and viscoelasticity. The instrument has a cam, a follower arm, a flat spring, a plate fixture, and a removable plate assembly. The cam is a rotating circular disk with a spiral slot. A cam follower on the follower arm resides in the spiral slot so that the follower arm pivots about its fixed end as the cam rotates. The spring is attached to and collinear with the fixed end of the follower arm so that the spring pivots in the opposite direction as the follower arm. The sample surface component include a removable plate assembly with a lower plate and an upper plate with mating sample surfaces on which test fluid is placed. The lower plate fits into a lower jaw of the plate fixture that is attached to the instrument base. The upper plate fits into an upper jaw of the plate fixture attached to the free end of the spring. A fluid is placed on the lower sample surface. The cam rotates, pushing the follower arm up, causing the spring to pivot down, and pressing the sample surfaces together. The cam is reversed, causing the spring to impart a separation force to the plates. The time it takes for the plates to separate is measured and converted to a viscosity value.

12 Claims, 9 Drawing Sheets

SAMPLE SURFACE COMPONENT FOR AN INSTRUMENT THAT MEASURES VISCOSITY AND VISCOELASTICITY

CROSS-REFERENCES TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The present invention relates to fluid measurements, more particularly, to an instrument for measuring the viscosity of fluids.

2. Description of the Related Art

It has been known that the viscoelasticity, or tackiness, of some bodily fluids change in response to bodily rhythms. For example, the cervical mucus and saliva of a female has a maximum fluidity just before ovulation, where ovulation is defined as the moment that an ovum is released from the follicle. This knowledge led to the applicant's previous activities in the development of techniques for monitoring the viscoelasticity, or tackiness, and other properties of cervical mucus and saliva as predictors of time of ovulation and to improvements in rheometer or viscometer apparatus for measuring such viscoelastic properties. See, for example, L. E. Kopito and H. J. Kosasky, "The Tackiness Rheometer Determination of the Viscoelasticity of Cervical Mucus," Human Ovulation, edited by E. S. E. Hafez, Elsevier, North-Holland Biomedical Press, 1979, pp. 351 et seq., S. S. Davis, "Saliva is Viscoelastic", Experientia, 26:1298, (1970), R. H. Davis et al., "Saliva Viscosity Reflects the Time of Ovulation", Experientia, 30:911, (1974), and U.S. Pat. Nos. 4,002,056 and 4,167,110.

It is also known that the normal viscoelasticity of some bodily fluids changes in response to abnormal body conditions. For example, in a newborn baby with cystic fibrosis, the meconium, the first bowel movement of a newborn, has a viscoelasticity approximately five times that of a baby without cystic fibrosis.

There are a number of devices available for measuring viscosity. The above-identified U.S. Pat. No. 4,779,627, in addition to disclosing a process for determining female ovulation time by measuring saliva viscoelasticity, discloses a device for measuring the viscoelasticity of the sublingual saliva. The device has a shape somewhat like a syringe, with an outer cup, an inner cup concentric with and located within the outer cup, and a plunger. A roughened surface on the end of the plunger holds the saliva sample. The plunger is inserted into the inner cup until the saliva sample is compressed against the bottom of the inner cup. A predetermined amount of weight pulls the inner cup downward, stretching the saliva sample. If the viscoelasticity of the saliva is low, the saliva sample will fracture, causing the inner cup to fall to the bottom of the outer cup. An indicator at the bottom of the outer cup indicates that the inner cup has fallen to the bottom, which, in turn, indicates that ovulation will soon take place. If, however, the viscoelasticity of the saliva is high, the saliva sample will hold the plunger and inner cup together so that the inner cup will not fall to the bottom, indicating that ovulation will not take place in the near future.

The main disadvantage of the device is that it must be taken apart in order to take a sample. The plunger must be removed from the inner cup before being inserted in the mouth to obtain a saliva sample. This has the potential for the person to easily contaminate the saliva sample by incorrectly reinserting the plunger after taking the sample, invalidating the measurement.

U.S. Pat. Nos. 5,640,968, 5,851,190, and 6,149,604 disclose handheld instruments for measuring saliva viscoelasticity. The instruments are designed specifically for saliva, which means that their range of measurement is very limited, and cannot measure the viscosity or viscoelasticity of dense fluids such as meconium.

BRIEF SUMMARY OF THE INVENTION

An object of the present invention is to provide an instrument that can measure a wide range of viscosities and viscoelasticities.

The viscosity and viscoelasticity measuring instrument of the present invention includes a housing within which the measuring mechanism resides. The components of the measuring mechanism include a cam, a follower arm, a spring, and a plate fixture. The cam is a vertical, circular disk with a spiral slot that is rotated by an electric stepper motor. A cam follower attached to the follower arm resides in the spiral slot so that, as the cam rotates, the follower arm pivots upwardly or downwardly about its fixed end. The spring is a flat, preferably metallic, strip, one end of which is attached to and collinear with the fixed end of the follower arm. Thus, the spring pivots in the opposite direction as the follower arm. The plate fixture holds a removable plate assembly that has three components, a lower plate, an upper plate, and a plate clip. The two plate components have mating sample surfaces on which the fluid to be tested is placed. The fixture has a lower jaw pivotally attached to the instrument base and an upper jaw pivotally attached to the free end of the spring. The pivoting attachments allow the plate sample surfaces to align as they come together during a test. The jaws have channels for receiving and holding the plates.

To perform a measurement, a fluid is placed on the lower sample surface. The cam rotates, pushing the free end of the follower arm upwardly, causing the follower arm to pivot about its fixed end. The spring, attached to the fixed end of the follower arm, rotates downwardly, pressing the sample surfaces of the upper and lower plates together. Then the cam is reversed, causing the spring to impart a separation force on the plates. The amount of time it takes for the plates to separate is measured and converted to a viscosity value. A strain gauge mounted to the spring indicates when the plates separate.

Other objects of the present invention will become apparent in light of the following drawings and detailed description of the invention.

BRIEF DESCRIPTION OF THE DRAWINGS

For a fuller understanding of the nature and object of the present invention, reference is made to the accompanying drawings, wherein.

DETAILED DESCRIPTION OF THE INVENTION

Figure 1:
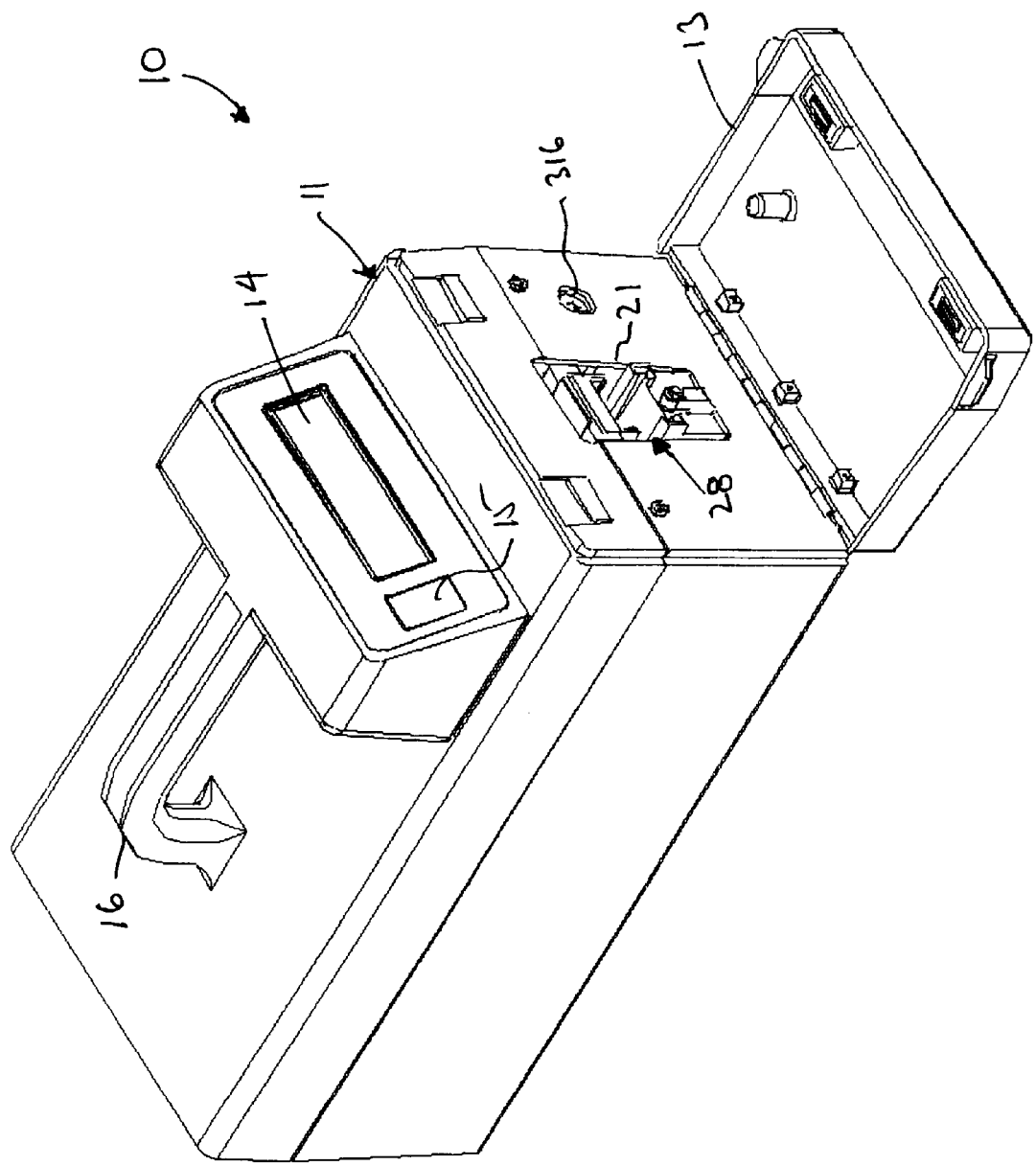
FIG. 1 is a perspective view of the front of the instrument of the present invention.

The basis of the viscosity and viscoelasticity measuring instrument of the present invention is that it is possible to determine the viscosity of a fluid by measuring the time it takes for the fluid to fracture under known conditions. The known conditions include the amount of force pulling the fluid apart, the area of the fluid over which the force is exerted, and the fluid temperature. In the present specification, unless otherwise indicated, the term "viscosity" refers to both viscosity and viscoelasticity.

The dynamic viscosity of a fluid sample is a function of the separation force, the area of one of the sample surfaces and the amount of time that it takes for the sample surfaces to separate. These values are related by the following equation:

$$\text{dynamic viscosity} = \frac{\text{separation force} * \text{separation time}}{\text{surface area}}$$

wherein the dynamic viscosity is calculated in poise (P), the separation force is measured in dynes (dy), the surface area is measured in square centimeters ($cm^2$), and the separation time is measured in seconds (s). The separation force/surface area is also called the shear stress. The kinematic viscosity is the dynamic viscosity divided by the density of the fluid and is in units of stokes (St). The customary unit of dynamic viscosity is the centipoise (cP) which has dimensions of $P \times 10^{-2}$, and the customary unit of kinematic viscosity is the centistoke (cSt) which has dimensions of $St \times 10^{-2}$.

Note that the equation is for viscosity, rather than for viscoelasticity. When using a Newtonian fluid, such as water, the equations will calculate pure viscosity. However, some fluid samples are non-Newtonian fluids. In a non-Newtonian fluid, there is an element of elastic recoil, or elasticity, along with the viscosity. Elasticity affects the separation time and separation force of the plates. Thus, the measurements used in the above equation are affected by the elasticity of the fluid sample. Because there is no specific equation for viscoelasticity, the equation for viscosity is used, and the viscoelasticity is measured in viscosity-equivalent units, giving a Newtonian equivalent of the combination of viscosity and elasticity found in a non-Newtonian fluid sample.

The portions of the determined viscoelasticity attributed to the viscosity and to the elasticity depend upon the thickness of the fluid sample (density, not breadth). As the thickness increases, the portion attributed to viscosity increases as a percentage of the viscoelasticity. For example, in a very thick saliva, the proportion of viscosity to elasticity may be 80% to 20%, while in a very thin saliva, the proportion may be 20% to 80%.

Another factor to consider is that, not only do the proportions of viscosity and elasticity change as a fluid thickens, but the absolute values of the viscosity and elasticity also change. For example, a thick saliva may have 80% of its viscoelasticity attributed to viscosity and 20% attributed to elasticity with absolute numbers of 64 cSt attributed to viscosity and 16 cSt attributed to elasticity, and a thin saliva may have 20% of its viscoelasticity attributed to viscosity and 80% attributed to elasticity with absolute numbers of 5 cSt attributed to viscosity and 20 cSt attributed to elasticity.

Figure 3:
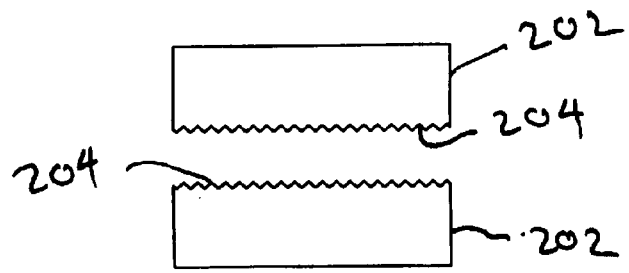
FIG. 3 is a front elevational view of two measurement plates.
Figure 4:
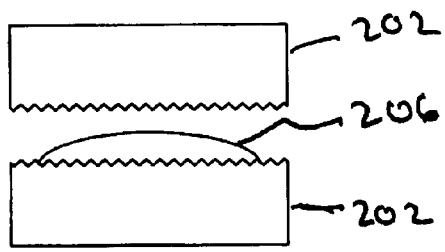
FIG. 4 is a front elevational view of the measurement plates of FIG. 3 with a fluid sample.
Figure 5:
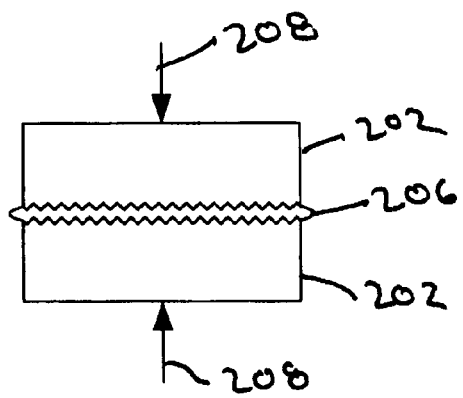
FIG. 5 is a front elevational view of the measurement plates of FIG. 3 pressed together.
Figure 6:
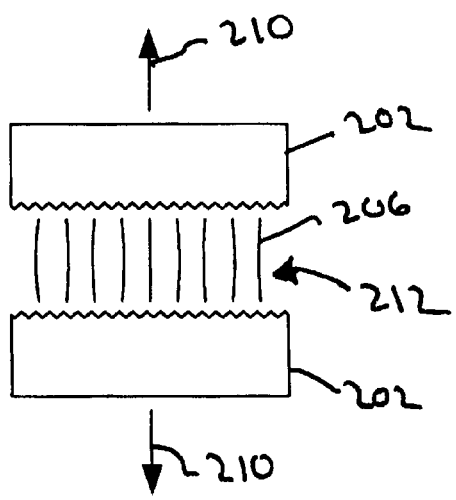
FIG. 6 is a front elevational view of the measurement plates of FIG. 3 separating after pressure is released.

FIGS. 3–6 show the physical process by which the viscosity of a fluid is measured. In FIG. 3, a pair of plates 202 having sample surfaces 204 are spaced apart. In FIG. 4, a fluid sample 206 of adequate volume is placed between the sample surfaces 204. In FIG. 5, the plates 202 are pressed together with a predetermined compression force 208. The compression force 208 must be large enough so that the fluid sample 206 coats the entire area of the sample surfaces 204. In FIG. 6, the plates 202 are pulled apart by a separation force 210 until the fluid sample fractures, as at 212. Fracturing occurs when the cohesion of the fluid sample 206 is overcome, where cohesion is defined as the tendency of parts of a body of like composition to hold together.

Measuring the viscosity of a fluid sample relies on the adhesion of the fluid sample to the sample surfaces where adhesion is defined as the tendency, due to intermolecular forces, for matter to cling to other matter. In order to have a valid measurement, the force of adhesion of the fluid sample to the sample surfaces must be greater than the force of cohesion of the fluid sample so that the fluid sample fractures before it separates from one of the sample surfaces. Therefore, sample surfaces having a force of adhesion for the fluid sample that is greater than the force of cohesion of the same fluid sample must be employed.

The action represented by FIG. 6 implies two ways of measuring: (1) using a known separation force 210 and measuring the time it takes for the fluid sample 206 to fracture, or (2) using a known separation time and measuring the amount of separation force 210 needed to fracture the fluid sample 206. The instrument of the present invention indirectly employs the former. The equation above for dynamic viscosity implies that the separation force, separation time, and surface area must be known in order to calculate the viscosity. The instrument of the present invention, however, does not rely upon knowing the absolute values of the separation force and surface area, only that these values remain consistent from measurement to measurement. This is accomplished by characterizing the instrument to determine the separation time for fluids of known viscosities. For example, the characterization procedure will measure the separation times for fluids of known viscosities, then interpolate and extrapolate from these measurements to create a table mapping separation times to viscosities. Alternatively, the viscosity is calculated from the separation time by an equation and the characterization data is used to scale the calculation for the particular instrument.

Figure 2:
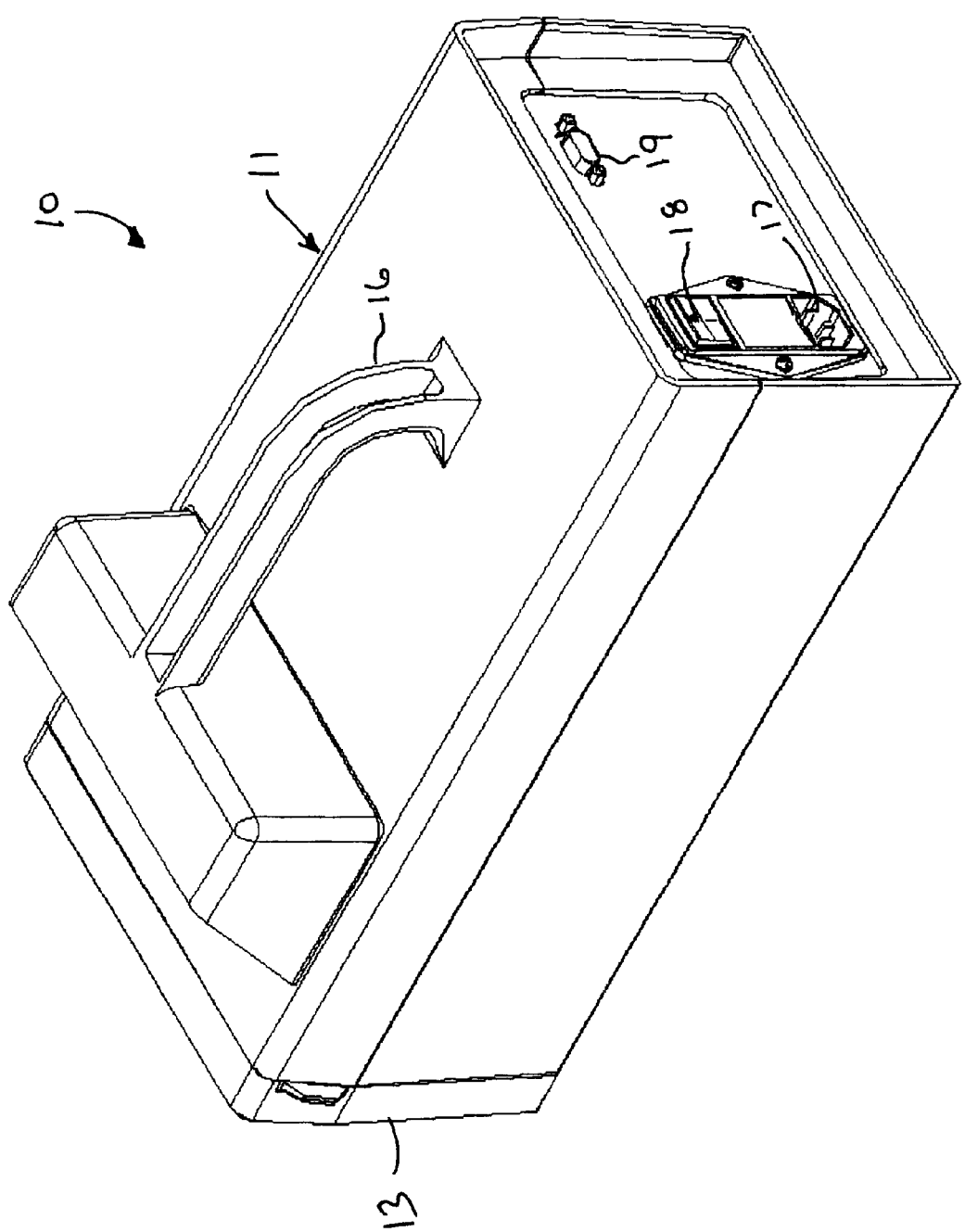
FIG. 2 is a perspective view of the rear of the instrument of the present invention.

The current external configuration of the viscosity measuring instrument 10 of the present invention is shown in FIGS. 1 and 2, keeping in mind that the design shown is merely illustrative, and that any design that is able to perform the necessary functions is contemplated. Externally, the instrument 10 includes a housing 11, a door 13, a visual display 14, a characterization switch 15, a handle 16, a power input plug 17, and power switch assembly 18, and an optional external communications port 19. The purposes of the housing 11, handle 16, power input 17, and power switch 18 are obvious. The door 13 is hinged downwardly and provides access to the operator for inserting the removable plate assembly 30, as described below. The visual display 14 both instructs the operator and informs the operator as to the status of the instrument 10 and the test results. The present invention also contemplates that there may not be an internal display, and that the instructions, status, and results will be sent to an external computer for display. The characterization switch 15 instructs the instrument 10 to perform an instrument characterization, as described below. The optional external communications connector 19 provides a means for an external computer to receive setup parameters and test results and, optionally, to control the operation of the instrument 10.

Figure 7:
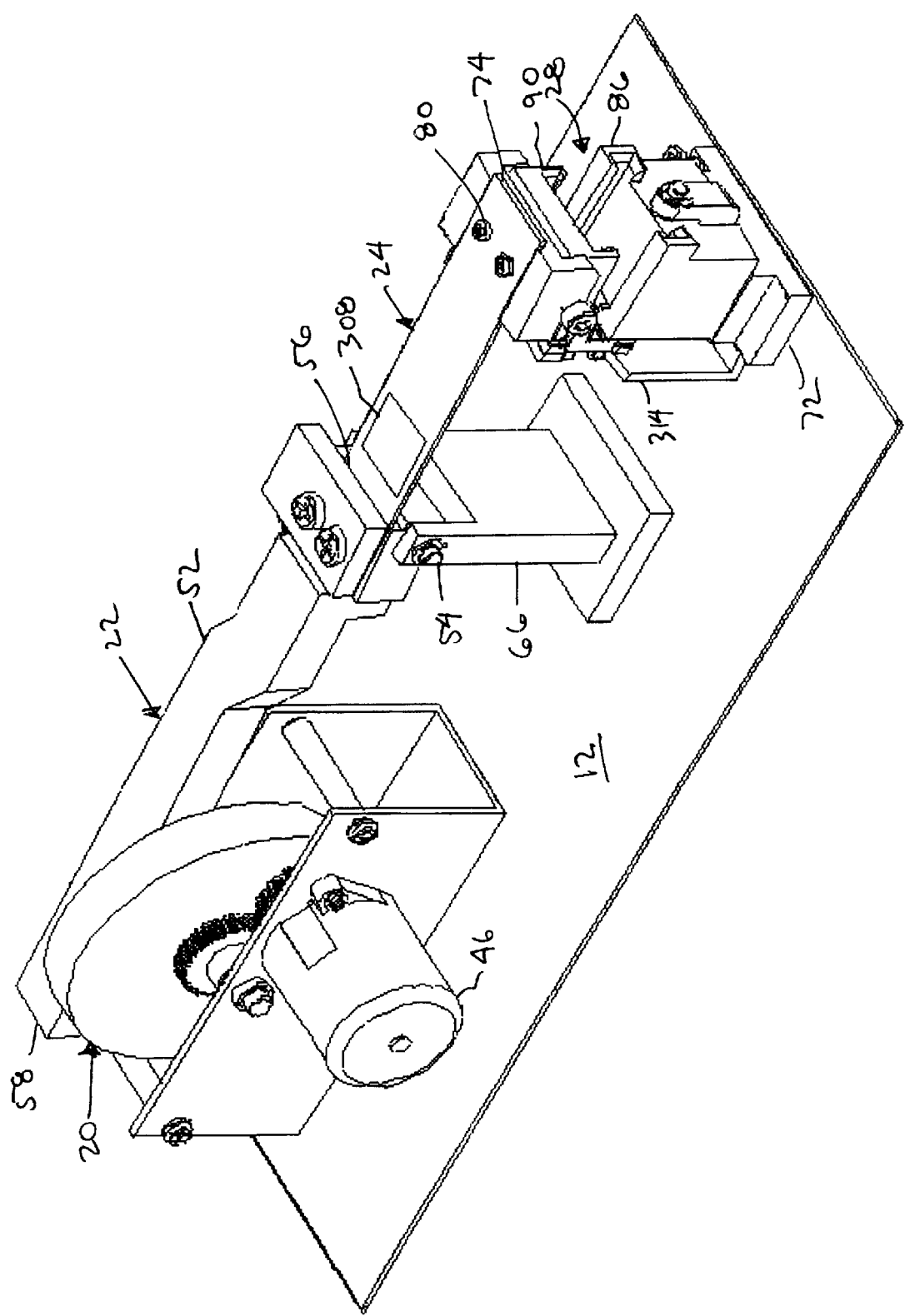
FIG. 7 is a perspective view of the instrument of FIG. 1 with the cover removed.
Figure 8:
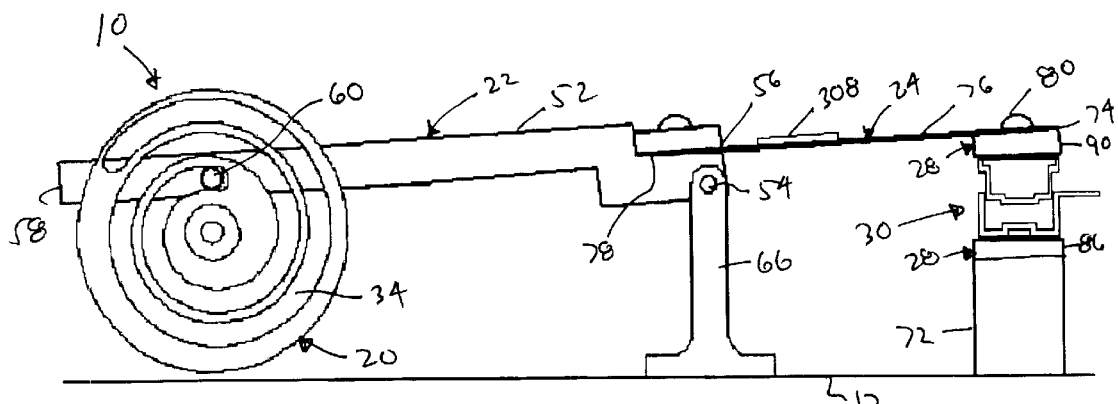
FIG. 8 is a side view of the instrument of FIG. 7 in its resting state.

The internal mechanical components of the instrument 10, shown in FIGS. 7 and 8, include a cam 20, a follower arm 22, a spring 24, and a plate fixture 28. In brief, a fluid for test is placed on the test surface 114 of the lower plate 104 of the plate assembly 30 and the test is started. The cam 20 rotates, pushing the free end 58 of the follower arm 22 upwardly, causing the follower arm 22 to pivot about the fixed end 56. The spring 24, attached to the fixed end 58 of the follower arm 22, rotates downwardly, pressing the two components of the plate fixture 28 together. The plates 102, 104 of the removable plate assembly 30, which are held by the plate fixture 28, are pressed together. When the compression force reaches a predetermined level for a predetermined period of time, the cam 20 is reversed, eventually causing the spring 24 to impart a separation force on the plates 102, 104. The amount of time it takes for the plates 102, 104 to separate is measured. The time measurement is converted to a viscosity value representing the viscosity of the sample fluid either through a lookup table or an equation.

Figure 11:
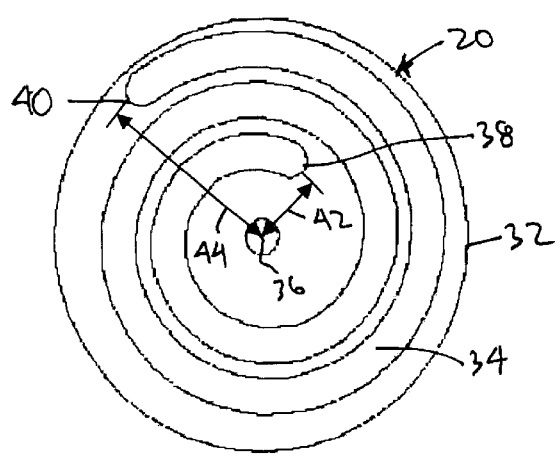
FIG. 11 is a view of the cam of FIG. 7.

The cam 20, shown in detail in FIG. 11, is a circular disk 32 with a spiral slot 34. In the illustrated configuration, the slot 34 is approximately 0.255" inches wide. The slot 34 encircles the center 36 of the disk 32, starting at an inner end point 38 with a radius of approximately 0.587", as at 42. As the slot 34 extends around the disk center 36, its distance from the disk center 36 increases by slightly more than 0.001" per degree of arc. The slot 34 extends for a distance equal to about 781° of arc, until its outer end point 40 has a radius of approximately 1.377", as at 44. Thus, the radius of the slot increases by 0.790" over 781° of rotation. The absolute radii of the inner end point 38 and outer end point 40 are not important as long as the distance between the two radii is as required for the particular embodiment of the instrument, in this case, 0.790".

The cam 20 is mounted vertically such that, as the disk rotates, a cam follower within the slot will be displaced from the center 36 of the disk 32 a distance of 0.001" per degree of rotation of the cam 20. Obviously, whether the cam follower moves toward or away from the disk center 36 depends upon the direction of rotation of the cam 20. In the orientation of FIG. 11, the cam follower displaces upwardly as the cam 20 rotates clockwise. The maximum displacement for the illustrated configuration is 0.790", the radial difference between the end points 38, 40 of the slot 34.

The above-described cam 20 is but one possible configuration. Depending upon the design of other components of the instrument, different cam configurations may be used to effect testing of different ranges of viscoelasticity.

The cam 20 is rotated by an electrical stepper motor 46. A set of reduction gears 48 reduces the rotational speed of the motor 46 as appropriate for the present invention. Any combination of the various motors 46 and reduction gears 48 known in the art that provides an appropriate step resolution and torque may be used. In the present embodiment, a 7.5° stepper motor is employed.

The follower arm 22 is a bar 52 with a rotational mount 54 at the fixed end 56 and a cam follower 60 at the free end 58. The rotational mount 54 permits the free end 58 to pivot up and down. The cam follower 60 seats within the cam slot 34 so that, as the cam 20 rotate forwardly (clockwise), the free end 58 pivots upwardly and as the cam 20 rotates in reverse, the free end 58 pivots downwardly. Optionally, the cam follower 60 is rotatably mounted to the bar 52 to reduce friction while moving within the cam slot 34. In the illustrated embodiment, the dimensions of the cam 20 and follower arm 22 are such that the follower arm 22 pivots by 3.8° when the cam 20 is rotated by 370° and by 7.8° when the cam 20 is rotated by 780°. This equates to the follower arm 22 pivoting by slightly more than 0.01° per degree of cam rotation. To achieve this displacement, the distance between the rotational mount 54 and cam follower 60, when used in conjunction with the above example cam dimensions, is 5.74".

The spring 24 is a flat strip 76 attached at one end 78 to the fixed end 56 of the follower arm 22 such that the spring 24 is approximately collinear with the follower arm 22. The spring 24 has a free end 74 remote from the follower arm 22. The material of which the spring 24 is composed allows it to flex along its length. The spring 24 is designed to provide a maximum force in the range of 2–10 lbs with deflected by 4°. Currently, the spring 24 is composed of 0.080" thick Aluminum Alloy 2024 T3 per AMS 4307. A strain gauge 308, mounted to or integral with the spring 24, measures whether or not the spring 24 is under tension and exerting a force, either compression or separation.

Figure 12:
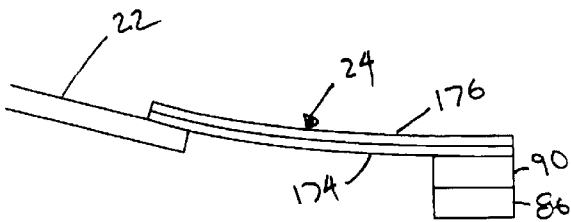
FIG. 12 is a side view of the main spring and leaf spring in compression mode.
Figure 13:
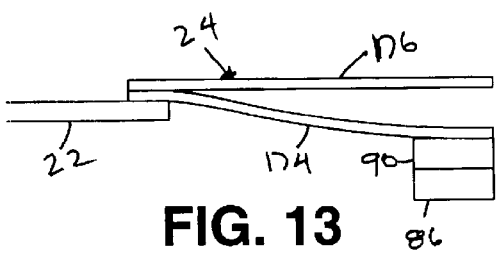
FIG. 13 is a side view of the main spring and leaf spring of FIG. 12 in separation mode.

In order to measure some fluids, it may be necessary to apply more compression force than separation force. The present invention contemplates that the spring 24 may include a main spring 174 overlapped by a leaf spring 176, as in FIGS. 12 and 13. When the spring 24 is in compression mode, as in FIG. 12, both the main spring 174 and leaf spring 176 apply the compression force to the plate fixture components 86, 90. When the spring 24 is in separation mode, as in FIG. 13, only the main spring 174 applies the separation force.

Figure 14:
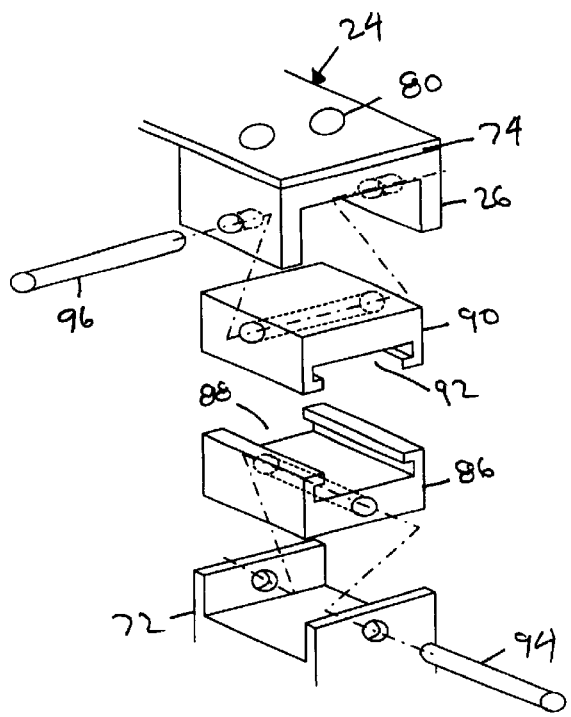
FIG. 14 is an exploded, partial phantom view of one configuration of the plate fixture of FIG. 7.
Figure 15:
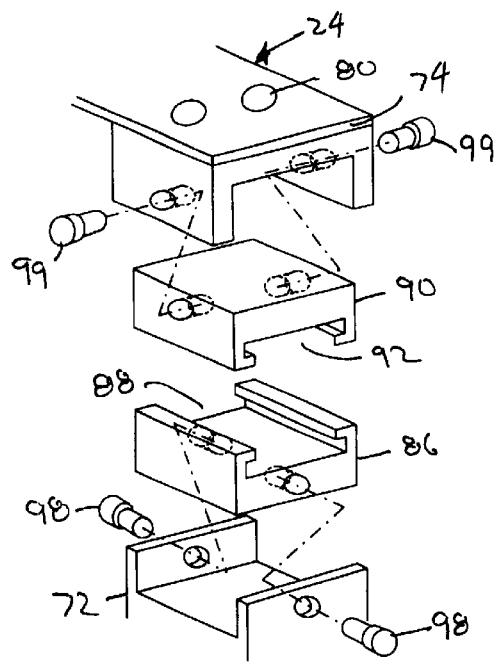
FIG. 15 is an exploded, partial phantom view of another configuration of the plate fixture of FIG. 7.

The fixture 28 holds the removable plate assembly 30. As shown in FIGS. 14 and 15, the fixture 28 has two jaw parts. The lower jaw 86 is fixed to the instrument base 12 by a pedestal 72 and is shaped to include a channel 88. The upper jaw 90 is fixed to the free end 74 of the spring 24, as at 80, and is shaped to include a channel 92. The cross-section of the channels 88, 92 is preferably rectangular, as shown in FIGS. 14 and 15, but can be any shape that performs as described below with reference to the removable plate assembly 30. The channels 88, 92 are open to receive the removable plate assembly 30, as described below.

If the jaws 86, 90 were rigidly fixed to the base 12 and spring 24, respectively, imperfections in the removable plate assembly 30 or perturbations in the motion of the spring 24 relative to the base 12 would mean that the sample surfaces 114, 128 of the plates 102, 104 may not meet squarely during plate compression. This could cause the fluid sample to distribute unevenly across the sample surfaces 114, 128, resulting in an inaccurate measurement.

To solve this problem, the jaws 86, 90 are pivotally attached, that is, they are attached in such a way that the plates 102, 104 can adjust themselves to align properly as the upper sample surface 128 touches the lower sample surface 114. In one configuration, shown in FIG. 14, the lower jaw 86 is pivotally attached to the pedestal 72 by an axle 94, which allows side-to-side pivoting of the lower jaw 86 relative to the pedestal 72. The upper jaw 90 is pivotally attached to the spring 24 by an axle 96, which allows front-to-back pivoting of the upper jaw 90 relative to the spring 24. In another configuration, shown in FIG. 15, the lower jaw 86 is pivotally attached to the pedestal 72 by a pair of screws 98, which allow side-to-side pivoting of the lower jaw 86 relative to the pedestal 72. The upper jaw 90 is pivotally attached to the spring 24 by a pair of screws 99, which allow front-to-back pivoting of the upper jaw 90 relative to the spring 24.

As shown in FIGS. 16–19, the removable plate assembly 30 has three components, the lower plate 102, the upper plate 104, and the plate clip 106. The lower plate 102 is generally rectangular open-top box 108. The sample surface 114 is located on the floor 110 of the box 108. The shape of the box 108, shown as generally rectangular in the figures, is only significant in that the floor 110 must be large enough to accommodate the required sample surface 114. The floor 110 extends outwardly from the box 108 on opposing sides to form a pair of rails 116. The rails 116 have the same cross-section as the lower jaw channel 88, so that the lower plate 102 slides into the lower jaw 88. Optionally, a tab 118 extends from the upper edge of the box 108 to provide a handle for an operator to grasp without contaminating the plates 102, 104. Optionally, there is an aperture 120 in one of the box walls to provide access to the sample surface 114 for depositing the fluid test sample, as in FIGS. 17 and 18.

Optionally, the plate assembly 30 includes a plate type identifier 122 for identifying to the controller which type of plate assembly 30 is installed in the instrument 10. In one configuration, the floor 110 extends beyond the box 108 as a ledge 126. The ledge 126 includes notches 124 to indicate to the controller which type of removable plate assembly 30 is currently being employed. The notches 124 are only one means for indicating the plate assembly type. Any other method known in the art that performs the same function is contemplated. Examples include bar codes, reflective spots, where fixed spots on the plate assembly are either reflective or non-reflective, and internal circuit connectors, where contacts on the surface of the plate assembly complete a circuit in the controller or not. The various plate types have to do with the measurement range to be employed by the instrument 10, as described below.

The upper plate 104 is a generally rectangular box 170 with the sample surface 128 on its underside face 130. The upper plate 104 is sized so that it fits within the lower plate box 108. The upper side edges of the box 170 extend outwardly to form a pair of rails 134. The rails 134 have the same cross-section as the upper jaw channel 92, so that the upper plate 104 will slide into the upper jaw 90. Optionally, the lower jaw channels 88 and lower plate rails 116 and the upper jaw channels 92 and upper plate rails 134 have different cross-sectional parameters so that the plate assembly 30 cannot be installed upside down.

Figure 16:
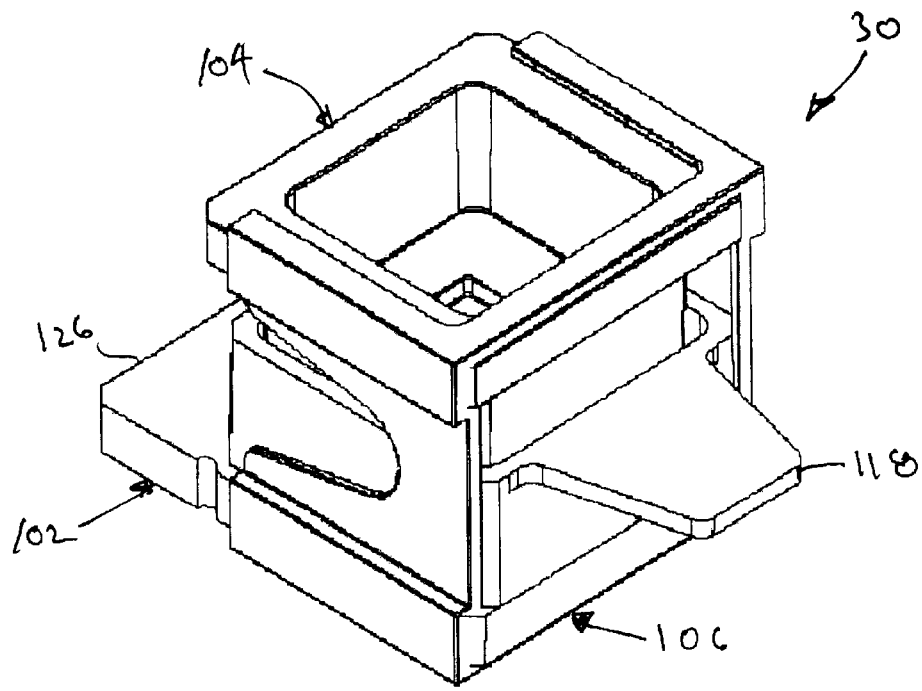
FIG. 16 is a perspective front view of one embodiment of the removable plate assembly.
Figure 17:
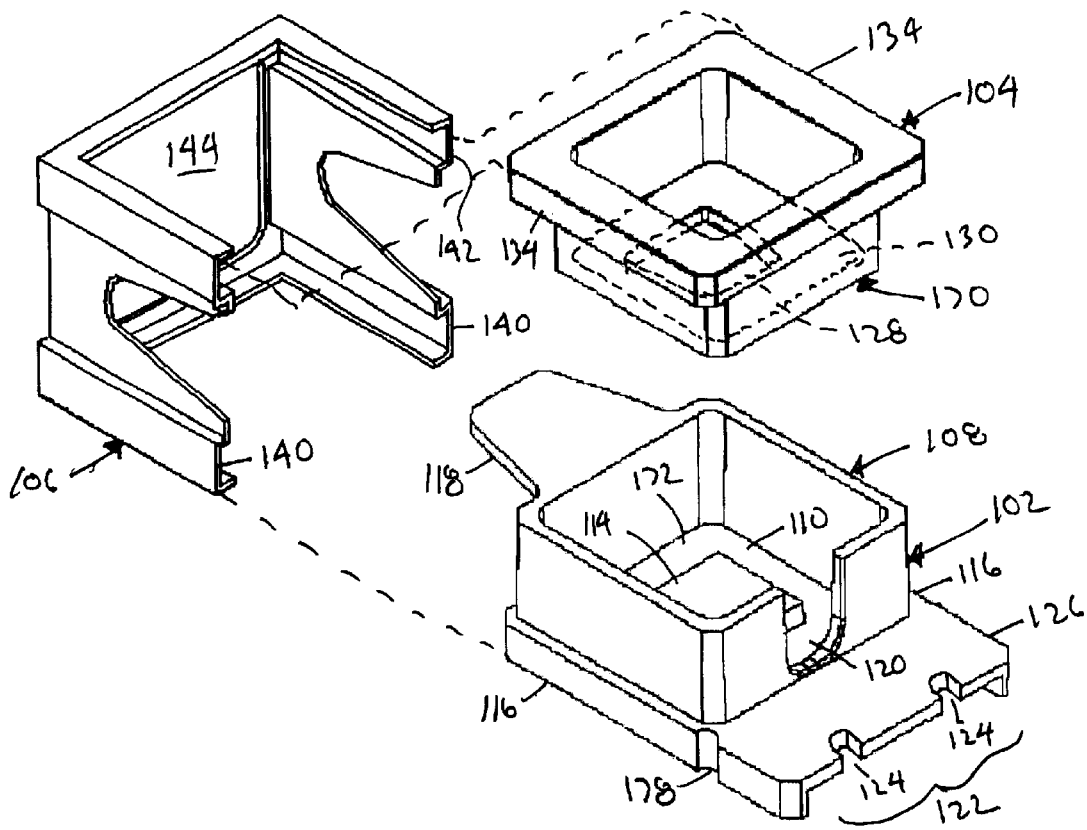
FIG. 17 is an exploded rear perspective view of the removable plate assembly of FIG. 16.
Figure 18:
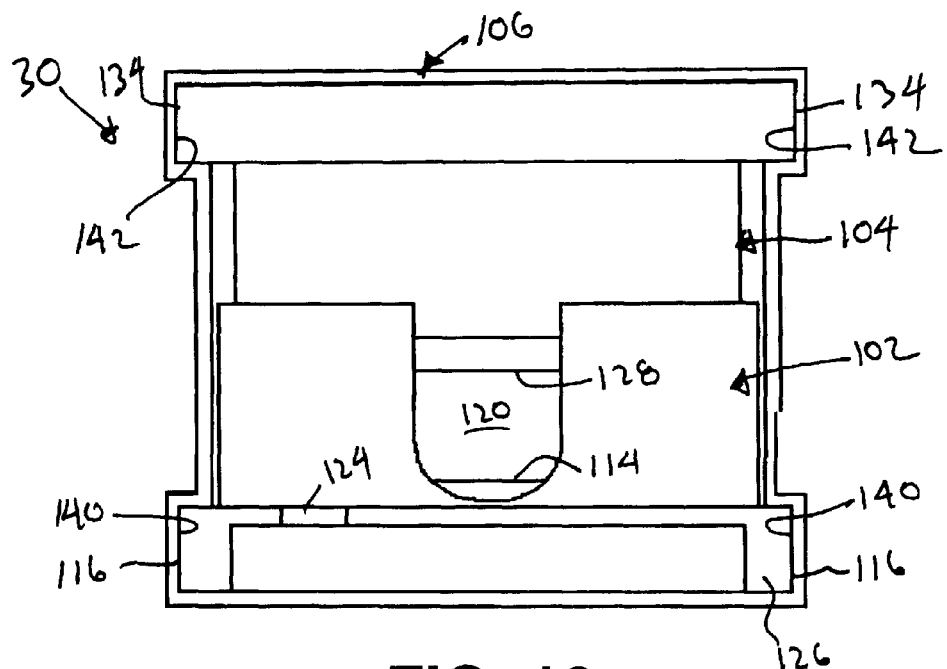
FIG. 18 is a rear view of the removable plate assembly of FIG. 16.
Figure 19:
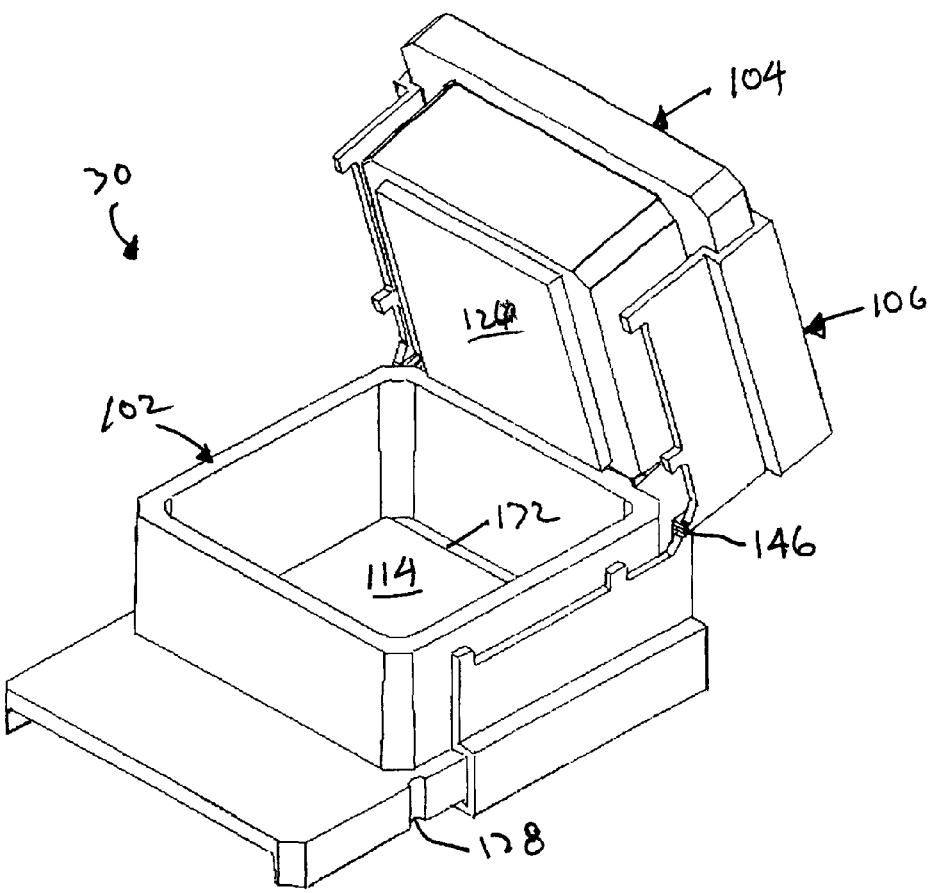
FIG. 19 is a perspective front view of a second embodiment of the removable plate assembly.

The plate clip 106 holds the lower plate 102 and upper plate 104 as one assembly temporarily prior to use. It prevents the sample surfaces 114, 128 from touching each other or becoming contaminated. The clip 106 has a pair of grooves 140, 142 into which the lower plate rails 116 and upper plate rails 134 fit, respectively. An opening 144 in the clip 104 provides a space for the tab 122 to fit through. In the embodiment of FIGS. 16 and 17, the clip 106 is rigid. In the embodiment of FIG. 19, the clip 106 has a hinge 146 between the lower grooves 140 and the upper grooves 142 so that the upper plate 104 can be pivoted away from the lower plate 102 to provide access to the sample surface 114 for depositing the fluid sample. The hinge 146 can be any type of hinge appropriate for the clip 106, such as, for example, a living hinge, ball in socket, or pin in cylinder. Hinges of these types are well known.

Optionally, the plate assembly 30 includes a means for retaining the plate assembly in the plate fixture 28 so that it stays in the fixture 28 when the clip 106 is being removed. The preferred method is to use a pair of depressions 178 in the lower plate rail 116 in conjunction with matching protrusions (not shown) in the lower jaw channel 88. As the lower plate 102 slides into the channel 88, the protrusion snaps into the depression 178. In another method, the rail and/or channel surfaces are roughened so that friction between the roughened surfaces retains the plate assembly 30 in the plate fixture 28. IN yet another method, a plate rail surfaces and channel surfaces are slightly skewed from each other so that as the plates slide into the jaws, they become wedged in the channels.

Figure 20:
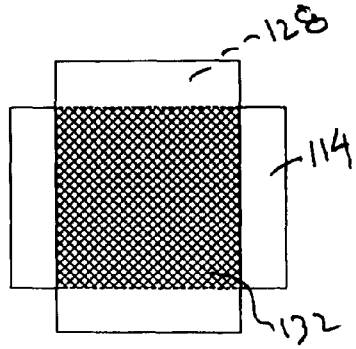
FIG. 20 is a top view of the overlapping sample surfaces of the removable plate assembly.

The present invention relies on several known conditions to test for viscoelasticity, one of which is that the surface area of the fluid sample is consistent, that is, that it does not change from test to test. As described above, the fixture jaws 86, 90 pivot so that the sample surfaces 114, 128 align when they make contact. It also means that, if the sample surfaces 114, 128 were exactly the size of the required sample fluid surface area, it is very likely that the sample surfaces 114, 128 would move laterally relative to each other a small amount. As a result, the sample surfaces would not precisely mate, so that the actual sample surface area could vary from test to test. The current embodiment of the present invention solves this problem by making the sample surfaces 114, 128 rectangular and at right angles to each other. As shown in FIG. 20, the lower sample surface 114 is rectangular, extending side to side, and the upper sample surface 128 is rectangular, extending front to back. Thus, when the sample surfaces 114, 128 mate, there is an overlap that creates a contact area 132 of consistent and known size. As with other parameters of the test process, knowing the absolute size of the contact area 132 is not important. Thus, in this context, the phrase, "known size," means that the test method can rely on knowing that the contact area size remains consistent from test to test. In the current embodiment, that contact area is a square approximately 1.5 cm on a side.

The present invention contemplates the use of any other method that can ensure that the contact area remains consistent from test to test. One such other method uses sample surfaces of different sizes. Suppose, for example, that the upper sample surface 128 is larger than the lower sample surface 114 such that the entire lower sample surface 114 fits comfortably within the perimeter of the upper sample surface 128. Then, when the sample surfaces 114, 128 mate, the contact area 132 will be the same size as the lower sample surface 114, a known size, even if the sample surfaces 114, 128 shift laterally relative to each other a small amount.

Preferably, the lower sample surface 114 is raised from the floor 110, creating a trench 172 around the sample surface 114,. Excess sample fluid squeezed out from between the sample surfaces 114, 128 during the measurement flows downwardly into the trench 172 away from the lower sample surface 114 so as to not affect the measurement.

Referring again to FIGS. 3–6, the measurement of viscoelasticity relies on the adhesion of the fluid sample 206 to the sample surfaces 204, where adhesion is defined as the tendency, due to intermolecular forces, for matter to cling to other matter. In order to have a valid measurement, the force of adhesion of the fluid sample 206 to the sample surfaces 114, 128 must be greater than the force of cohesion of the fluid sample 206 so that the fluid sample 206 fractures before it separates from one of the sample surfaces 204. Therefore, sample surfaces 204 having a force of adhesion for the fluid sample 206 that is greater than the force of cohesion of the fluid sample 206 must be provided. And, in general, the greater the viscoelasticity of a fluid, the greater the sample surface area needs to be so that the fluid fractures before it separates from the sample surface.

The adhesion of the fluid sample 206 to a sample surface 204 occurs over the entire area over which the fluid sample 206 and sample surface 204 make contact. So, the larger the contact area, the proportionally greater will be the adhesion of the fluid sample 206 to the sample surfaces 204.

One way to increase the area of the sample surface 204 is to increase the outer dimensions of the sample surface 204. However, the instrument 10 of the present invention is intended to test a very wide range of viscoelasticities which cannot be accommodated by a single size of sample surface. This means that, for different test ranges, different sample surface areas are needed. Opposing this requirement are the practical aspects of the instrument for ease of use and manufacture of the instrument, where it is desired that the removable plate assembly 30 be the same size, regardless of the range of viscoelasticities to be tested, so that the plate fixture 28 does not have to change.

To solve this problem, the preferred way to increase the area of the sample surface 204 is to roughen the surfaces so that there are a plurality of valleys extending into the sample surface 204. The surface to which the fluid sample 206 adheres then includes the area covered by the walls of any valleys extending into the sample surface 204 to which the fluid sample 206 can come into contact. Roughening the sample surface 204 provides a greater sample surface area without increasing the outer profile of the sample surface 204. And different viscoelasticity ranges can be accommodated by different degrees of roughness.

Figure 21:
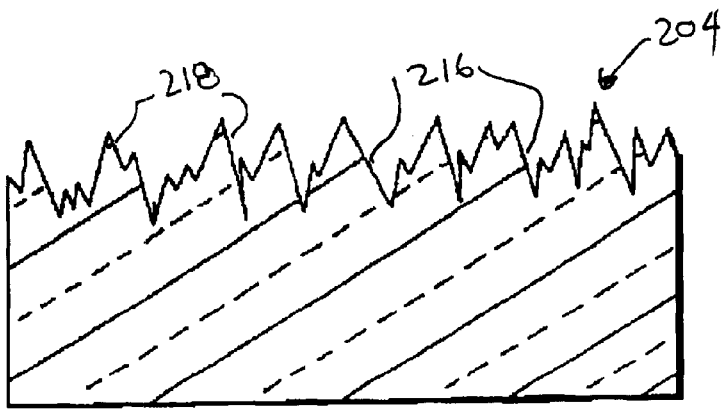
FIG. 21 is an enlarged cross-sectional view of a roughened sample surface.

A roughened sample surface 204 is composed of a random distribution of irregularly shaped valleys 216 and peaks 218, as shown in FIG. 21. There are two basic parameters that are important in characterizing the sample surface 204 when used in an instrument for measuring viscosity. The first of these parameters is the average depth of the valleys 216, as measured from the plane defined by the tops of the peaks 218. The preferred range of this average is from 10 picometers (pm) to 100 micrometers ($\mu$m), and the most preferred range is from 50 $\mu$m to 80 $\mu$m.

The second parameter is the amount of valley area, the sum of the surface area of the valley walls below one half of the average depth of the valleys, relative to the total surface area. The preferred range of valley area is from 35% to 65% of the total surface area, and the most preferred range is from 45% to 55%.

If the average depth of the valleys 216 is too shallow, such as less than 10 pm, the sample surface 204 will be too smooth and will not work adequately because the area of the sample surface 204 will be so small that the fluid sample will not adhere with a force greater than the cohesion of the fluid sample. As explained above, if the force of adhesion is smaller than the force of cohesion of the fluid sample, the fluid sample will separate from the sample surface 204 before it fractures.

If the average depth of the valleys 216 is too great, such as greater than 100 $\mu$m, or the ratio of valley area to total area is too large, such as greater than 65%, the surface will also not work adequately because the fluid sample would spread into the deep or large valleys 216, leaving the amount of fluid sample remaining outside the valleys 216 too small for an accurate measurement. If the fluid sample is too small, it will not cover the entire area of the sample surface 204, resulting in an inaccurate value for the fracturing surface area, and rendering the calculated viscosity inaccurate.

If the ratio of valley area to total area is too low, such as less than 35%, the sample surface 204 will also not work adequately because the area of the sample surface 204 will be so small that the fluid sample will not adhere with a force greater than the cohesion of the fluid sample. As explained above, if the force of adhesion is smaller than the force of cohesion of the fluid sample, the fluid sample will separate from the sample surface 204 before it fractures.

The plates 104, 106 and, as a result, the sample surfaces 114, 128, are composed of a rigid plastic. Currently, the preferred material is Grilamid TR55, a nylon 12. Preferably, the plates 104, 106 are produced by molding rather than grinding or blasting. A mold with particular surface characteristics etched into it can be created and used to form sample surfaces with consistent surface topology and size. Although no two molded surfaces can be exactly alike, the differences from one surface to the next will not be nearly as great as the difference from one ground or blasted surface to the next, resulting in better repeatability of the measurements.

The purpose of the instrument 10 of the present invention is to measure viscosity of fluids, and any contamination of the sample surfaces 114, 128 will result in erroneous test results. In order to protect the sample surfaces 114, 128 from contamination and to maintain a dry environment because of the intensely hygroscopic nature of the plate material, the removable plate assembly 30 is packaged in a vacuum-sealed pouch as a final step in manufacture. The plate assembly 30 is removed from the pouch prior to use.

Figure 22:
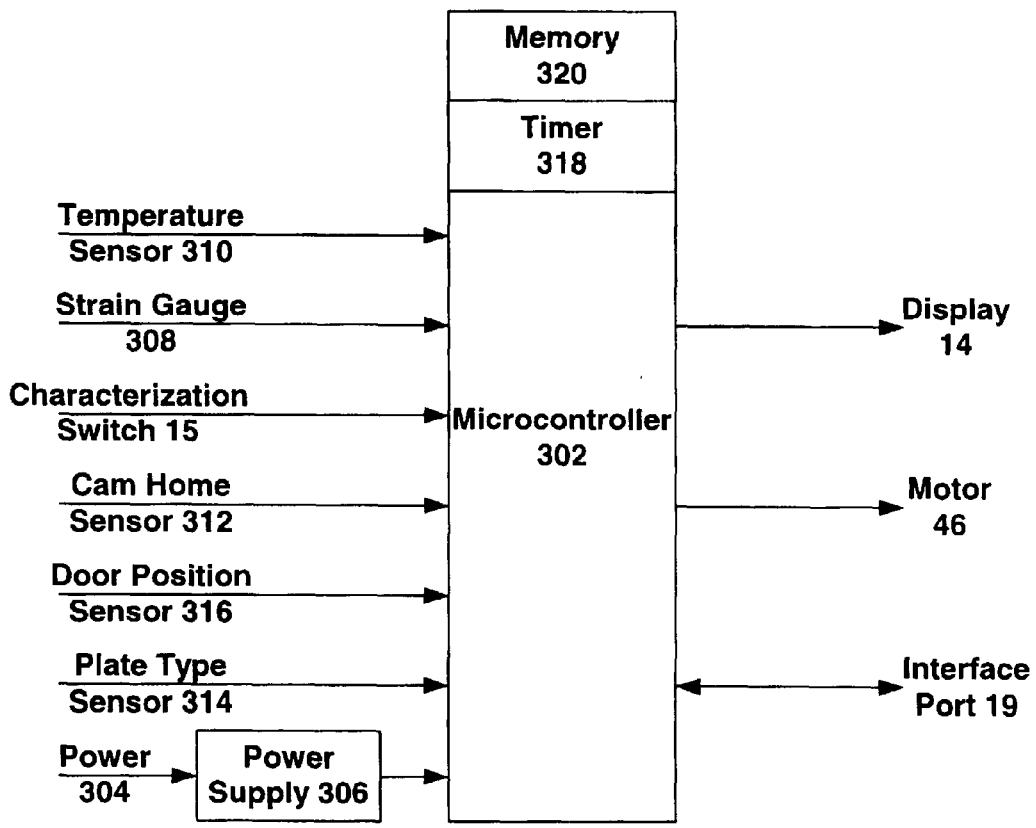
FIG. 22 is a block diagram of the electronic control circuit of the present invention.

The instrument 10 has a controller, a block diagram of which is shown in FIG. 22. The controller is based around a microcontroller ($\mu$C) 302 programmed to perform the necessary functions. Power is supplied via a wall plug 304 and power supply 306, the design of which is well-known in the art. Input signals to the $\mu$C 302 include the strain gauge 308, a cam home sensor 312, a plate type sensor 314, a door position sensor 316, a characterization switch 15, and an optional temperature sensor 310. There are several different ways known in the art to implement each of these various inputs. The following description is only an example of one way to implement the signals and is not intended to preclude the use of others that provide the same results.

Figure 10:
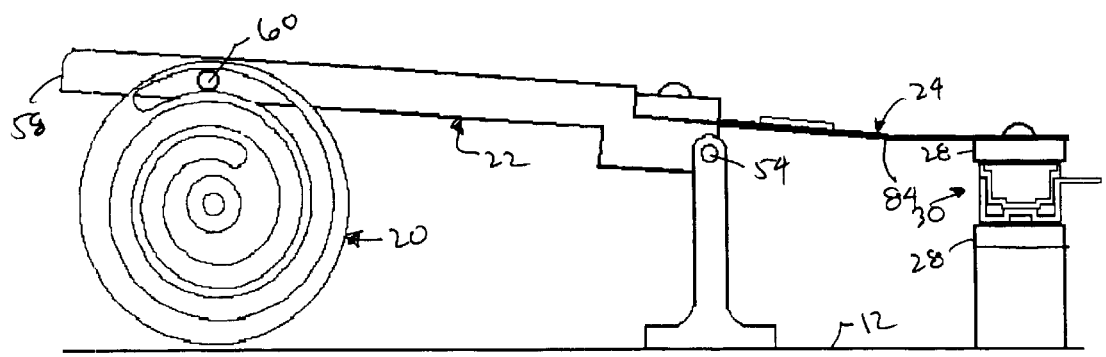
FIG. 10 is a side view of the instrument of FIG. 7 in its second operative state.

The strain gauge 308 is positioned on the spring 24 and is used to determine whether or not the spring 24 is under tension. As in FIG. 10, when the fixture arm 26 reaches its travel limit, the spring 24 begins to deform, which is sensed by the strain gauge 308. Conversely, when the fluid sample fractures, the strain gauge 308 registers the occurrence by sensing the removal of tension on the spring 24.

The cam home sensor 312 informs the μC 302 when the cam 20 is in its home position. This is the position where the removable plate assembly 30 can be inserted into the fixture 28 and is the starting point for the test, as described below. The cam home sensor 312 can be any type of switch that is adequate to the task, including a mechanical switch, optical sensor, magnetic sensor, etc. It is expected that the physical position of the cam home sensor 312 sensor will be adjustable so that the home position of the cam 30 can be calibrated for each instrument.

The plate type sensor 314 reads the plate type identifier 122 on the plate assembly 30. The form of the plate type sensor 314 depends on how the plate type identifier 122 is implemented. For example, if the plate type identifier 122 includes notches 124, as shown in FIG. 17, the plate type sensor 314 can be a pair of optical sensors, each positioned to straddle the location of one of the notches 124. Whether a notch 124 is present registers on the optical sensor, which forwards the reading to the μC 302. The μC 302 is programmed to interpret the existence of two notches as meaning that no plate assembly 30 is installed. This means that a plate assembly 30 can have only one notch or no notches. Note that there may be any number of notches 124 and the appropriate number of sensor elements. For other implementations of the plate type identifier 122, other forms of the plate type sensor 314 can be used.

The door position sensor 316 indicates to the μC 302 whether or not the housing door 13 is open or closed, the purpose of which is described below. In the current implementation, this sensor 316 is a mechanical switch.

The characterization switch 15 resides on the front of the instrument 10 and is used by the operator to instruct the apparatus to perform an instrument characterization. In the current implementation, the characterization switch 15 is a mechanical switch.

The optional temperature sensor 310 measures the ambient temperature. The viscosity of a body fluid is affected by the fluid's temperature. So the temperature sensor 310 may be used to determine the approximate temperature of the test sample in order to account for temperature in the viscosity measurement. The temperature sensor 310 itself can be any temperature sensor known in the art, including resistive, capacitive, mechanical, etc.

In its current configuration, the μC 302 has two outputs: a visual display 14 and control signals for the cam motor 46. In the current implementation, the display 14 is of the liquid crystal type (LCD) which is well-known in the art. Other typical display types include light-emitting diode (LED) and plasma. The motor control signals provide the signals required by the motor 46 to control direction and speed of rotation. The actual signals needed depend upon the motor 46 and are well-known in the art.

Optionally, the instrument 10 has an external communications port 19 for connection to an external computer or other device. Any communications protocol can be implemented as long as it is compatible with the expected external device. In the current implementation of the instrument 10, the well-known RS-232C protocol is employed.

Operation

Performing a test using the instrument 10 begins by removing the plate assembly 30 and a sampling syringe from their protective packages. A sample of the fluid to test is drawn into the syringe. In the embodiment of FIG. 17, the syringe is inserted into the lower plate aperture 120, or in the embodiment of FIG. 19, the upper plate 104 is pivoted away from the lower plate 102 to make the lower plate sample surface 114 accessible. The test fluid is injected onto the sample surface 114 of the lower plate 102, being careful not to contaminate the sample surfaces 114, 128. Next, the instrument door 13 is opened and the plate assembly 30 is installed in the plate fixture 28 through an opening 21 in the housing 11 such that the lower plate rails 116 and the upper plate rails 134 slide into the lower jaw channel 86 and upper jaw channel 88, respectively. As the plate assembly 30 is manually pushed into the plate fixture 28, the lower plate 102 and upper plate 104 slide out of the plate assembly clip 106. When the plates 102, 104 are completely installed in the plate fixture 30, the plate assembly clip 106 is no longer needed and is discarded. Alternatively, the test fluid is injected onto the sample surface 114 through the aperture 120 after the plate assembly 30 is installed in the plate fixture 28.

After installing the plate assembly 30, the operator closes the door 13, causing the door switch 316 to close, which instructs the μC 302 to begin the test. The μC 302 reads the plate type sensor 314 to determine if a plate assembly 30 is present and to set the measurement range. The instrument 10 is capable of a wide range of measurements. However, as described above, different viscosity ranges require different plate surface characteristics and, consequently, different measurement parameters. For example, the viscosity of saliva will generally be in the 0–50 cSt range. This means that a relatively rough surface will be required so that the plates do not separate too fast to measure accurately. In another example, the viscosity of meconium will generally be in the 10,000–40,000 cSt range, requiring a relatively smooth surface so that the plates separate within a reasonably short period of time.

Figure 9:
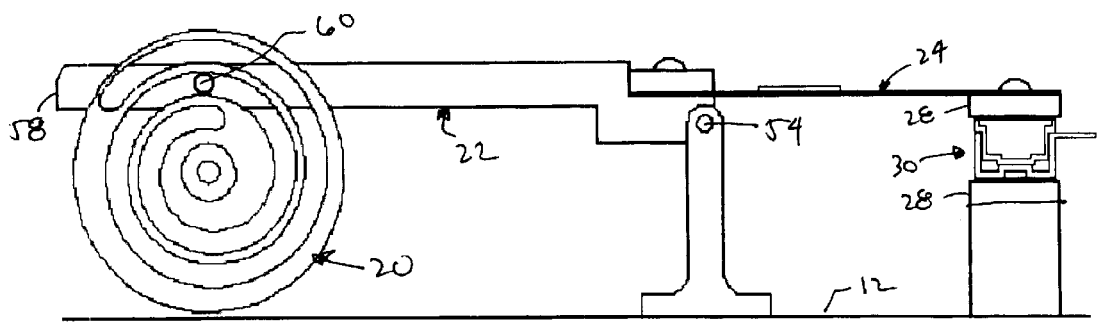
FIG. 9 is a side view of the instrument of FIG. 7 in its first operative state.

The different plate types affect two aspects of the test. It first affects the amount of pressure put on the plates by the instrument. See FIG. 5 and its associated text above. If too little pressure is used, the sample does not coat the sample surfaces sufficiently to provide an accurate test. Thus, the instrument 10 can adjust the amount of pressure applied to the plates based on the plate type. It does this by rotating the cam 20 a predetermined amount for the pressure desired. For all plate types, the cam 20 rotates until the spring 24 reaches its nominal travel limit, as described above with reference to FIG. 9. The amount of cam rotation beyond this depends upon the plate type. The farther the cam 20 rotates, the greater the compression force is on the plates 102, 104.

Secondly, the plate type affects how the measured separation time translates into a viscosity reading. For example, a separation time of 10 seconds may mean a viscosity of 20 cSt for a saliva sample with rough plates and a viscosity of 15,000 cSt for a meconium sample with smooth plates.

Once the plate type is determined, the μC causes the motor 46 to rotate the cam 20 the appropriate amount to apply the desired compression force to the plates 102, 104 for the desired amount of time. Then the μC rotates the cam 20 back to its home position, causing the spring 24 to exert a separation force on the plates 102, 104.

As indicated above, the separation force must remain consistent from measurement to measurement. Because the separation force is a function of the cam rotation, a predetermined cam rotation speed is necessary so that the separation force remains consistent. The characterization function, described below, is used to empirically determine the function for converting separation time into viscosity. Thus, the μC 302 does not need to know the actual amount of separation force in order to calculate the viscosity; it only needs to know that the separation force as a function of cam rotation is consistent.

Sometime between when the door 13 closes and the cam 20 reverses, the μC 302 starts a timer 318 and monitors the strain gauge 308. Once the strain gauge 308 informs the μC 302 that the plates 102, 104 have separated, the μC 302 reads the separation time from the timer 318. Where in the test cycle the timer 318 is started is not important, as long as it is before the separation force is applied to the plates 102, 104 and always at the same point during the test cycle. At this point, the μC 302 will typically convert the separation time into a viscosity measurement and present the result on the display 14.

The present invention contemplates two basic methods for converting the separation time into viscosity. The first uses a lookup table resident in μC memory 320. The separation time is used as an index into a table of viscosities. The value at the location indexed is the viscosity corresponding to the separation time. With this method, there may be one table for each plate type or there may be fewer tables with the μC 302 scaling the table output for the plate type. In the second method of converting the separation time into viscosity, the μC 302 mathematically calculates the viscosity from the separation time using an equation. Either conversion method and/or combinations of the two methods may be employed.

Characterization

The instrument 10 is characterized using standardized fluids of known viscosity. In the present implementation, three known fluids are used to establish a baseline for converting the separation time to a viscosity. The remainder of the conversion points are determined by interpolation and extrapolation.

The characterization procedure for the instrument of the present invention is essentially the same as the measurement procedure described above performed three times, once each with three fluids of known viscosity. In order to initiate a characterization, the operator presses the characterization switch 15. The μC 302 then begins the characterization procedure and optionally displays step-by-step instructions on the display 14. When characterization is complete, the instrument 10 returns to its normal operating mode.

The specifics of the characterization procedure, namely the fluids used, depend upon the expected measurement range. For example, if the measurement range in from 0–50 cSt, then the three fluids will be within the range of 0–50 cSt.

Thus it has been shown and described a viscosity measuring instrument for measuring the viscosity of a fluid which satisfies the objects set forth above.

Since certain changes may be made in the present disclosure without departing from the scope of the present invention, it is intended that all matter described in the foregoing specification and shown in the accompanying drawings be interpreted as illustrative and not in a limiting sense.

We claim:

1. A fluid sample surface plate assembly component adapted for use in an instrument for measuring the viscosity of a fluid sample, said instrument including a plate fixture for holding said plate assembly, said plate fixture including a lower jaw and an opposing upper jaw spaced from said lower jaw, said lower jaw having a lower channel and said upper jaw having an upper channel, said instrument including a means for moving said jaws closer together and farther apart, said component comprising:

(a) a lower plate including an open-top box with a floor, a lower sample surface on said floor, and a pair of opposed rails extending from said floor substantially parallel to said lower sample surface, said lower plate rails adapted for removably sliding into said lower jaw channel;

(b) an upper plate having an open-top box sized to fit within said lower plate box, said upper plate box having an underside face, a top edge, an upper sample surface on said underside face, and a pair of opposed rails extending from said top edge parallel to said upper sample surface, said upper plate rails adapted for removably sliding into said upper jaw channel;

(c) a plate clip having a pair of opposed lower grooves for removably receiving said lower plate rails and a pair of opposed upper grooves for removably receiving said upper plate rails, said clip temporarily holding said lower plate and said upper plate in fixed physical relationship to each other such that said sample surfaces oppose each other and are spaced apart; and (d) a means for providing access to said lower sample surface for depositing said fluid sample thereon;

(e) said sample surfaces being adapted for contiguous registration over a contact area with a fluid sample therebetween after said clip is removed, said fluid sample being in contact with each of said sample surfaces;

(f) said sample surfaces being textured such that, when said sample surfaces are pressed together and then pulled apart, the force of adhesion of said fluid sample to said sample surfaces is greater than the force of cohesion of said fluid sample.

2. The component of claim 1 wherein said sample surface texture includes each sample surface having a random distribution of valleys, said valleys having walls, the average depth of said valleys being in the range of from about 10 picometers to about 100 micrometers, and the total area of said valley walls below one half of said average depth being from 35% to 65% of the total area of said surface.

3. The component of claim 2 wherein said average depth is in the range of 50 micrometers to 80 micrometers.

4. The component of claim 3 wherein said total area of said valleys below one half of said average depth is between 45% and 55% of the total area of said sample surface.

5. The component of claim 1 wherein said plate assembly has a plate type that depends on said sample surface texture and said plate assembly includes a plate type identifier for identifying said plate type.

6. The component of claim 1 wherein said sample surfaces are sized such that the size of said contact area is known regardless of small lateral movements of said sample surfaces relative to each other as said sample surfaces are being pressed together.

7. The component of claim 6 wherein said sample surfaces are rectangular and orthogonal to each other.

8. The component of claim 1 wherein said lower sample surface is raised from said floor.

9. The component of claim 1 wherein said means for providing access to said lower sample surface includes an aperture in a wall of said lower plate box.

10. The component of claim 1 wherein said means for providing access to said lower sample surface includes providing said clip with a hinge between said lower grooves and said upper grooves such that said upper plate can be pivoted away from said lower plate.

11. The component of claim 1 wherein said plates are composed of a polymer.

12. The component of claim 11 wherein said sample surfaces are molded.

* * * * *